United States Patent [19]
Hsieh

[11] Patent Number: 5,608,776
[45] Date of Patent: Mar. 4, 1997

[54] METHODS AND APPARATUS FOR TWIN BEAM COMPUTED TOMOGRAPHY

[75] Inventor: Jiang Hsieh, Waukesha, Wis.

[73] Assignee: General Electric Company, Milwaukee, Wis.

[21] Appl. No.: 540,502

[22] Filed: Oct. 10, 1995

[51] Int. Cl.$^6$ ................................................. G21K 1/00
[52] U.S. Cl. ..................... 378/145; 378/146; 378/147; 378/149
[58] Field of Search ................................. 378/4, 145, 146, 378/147, 148, 149, 150, 151, 152, 153, 155, 159, 160, 19

[56] References Cited

U.S. PATENT DOCUMENTS

| | | | |
|---|---|---|---|
| 4,559,639 | 12/1985 | Glover et al. | 378/19 |
| 4,731,807 | 3/1988 | Plessis et al. | 378/147 |
| 4,991,189 | 2/1991 | Boomgaarden et al. | 378/4 |
| 5,054,041 | 10/1991 | Hampel | 378/4 |
| 5,231,654 | 7/1993 | Kwasnick et al. | 378/147 |
| 5,231,655 | 7/1993 | Wei et al. | 378/147 |
| 5,293,417 | 3/1994 | Wei et al. | 378/147 |
| 5,485,493 | 1/1996 | Heuscher et al. | 378/4 |

*Primary Examiner*—Don Wong
*Attorney, Agent, or Firm*—John S. Beulick; John H. Pilarski

[57] ABSTRACT

Methods and apparatus for performing a computed tomography scan are described. In one embodiment of the apparatus, a twin beam computed tomography scanner includes a beam splitter, an x-ray source for generating an x-ray to be projected generally towards, and at least partially through, an object, and a detector array comprising a plurality of detector cells arranged to form at least two cell rows. The beam splitter is positioned so that the x-ray projected from the x-ray source is substantially split to form at least two beams prior to being projected at least partially through the object.

17 Claims, 3 Drawing Sheets

333,608,776

METHODS AND APPARATUS FOR TWIN BEAM COMPUTED TOMOGRAPHY

FIELD OF THE INVENTION

This invention relates generally to computed tomography and, more particularly, to a twin beam computed tomography system including a pre-patient beam collimator.

BACKGROUND OF THE INVENTION

Computed tomography systems typically include an x-ray source which emits a fan beam directed through an object to be imaged and received by an x-ray detector array. The x-ray source and detector array are orientated to lie within an x-y plane of a Cartesian coordinate system, generally referred to as the "imaging plane". The x-ray source and detector array may be rotated together on a gantry within the imaging plane and around the image object, i.e., around the z-axis of the Cartesian coordinate system. Rotation of the gantry changes the angle at which the fan beam intersects the imaged object, and such an angle is generally referred to as the "gantry" angle.

The detector array has a plurality of detector elements, and each detector element generates a signal indicative of the intensity of transmitted radiation received by the detector element. At each gantry angle, such detector element signals are collected, digitized and saved. Such data sometimes is referred to as projection data. Intensity signals from each of the detector elements for a particular gantry angle may, for example, be stored in a projection data array. The gantry is rotated to a number of gantry angles and projection data is collected at each such gantry angle to form a tomographic projection set.

Each acquired tomographic projection set may be stored for later processing to reconstruct a cross sectional image, or slice, according to algorithms known in the art. The reconstructed image may be displayed on a conventional CRT tube or may be converted to a film record by means of a computer controlled camera.

The x-ray source is ordinarily an x-ray "tube" which includes an evacuated glass x-ray envelope containing an anode and a cathode. X-rays are produced when electrons from the cathode are accelerated against a focal spot on the anode by applying a high voltage across the anode and cathode. The voltage applied across the anode and cathode, the current flowing between the anode and cathode, and the duration of the exposure, for a given x-ray procedure, is generally referred to as the "exposure technique".

To increase the amount of projection data which may be collected during a scan, it is known to utilize two adjacent rows of detector elements. Specifically, the detector elements may be positioned side-by-side in two adjacent rows, and the x-ray source may be aligned with the detector array so that the output x-ray may be substantially simultaneously received by detector elements in both rows. A collimator typically is positioned at the interface between two detectors elements in respective rows. Such an apparatus sometimes is referred to as a "twin beam scanner".

The detector array may have ionization type detector elements or solid state detector elements as are known in the art. Both detector element types exhibit changes in their sensitivity to x-rays as a function of the position of the fan beam along their surface. Such changes in signal strength during the acquisition of a tomographic projection set may produce undesirable ring like image artifacts in the resultant reconstructed image.

For example, the sensitivity response of known detector elements at the detector element edge region is low. As a result, the detector element may not generate a highly accurate intensity signal for x-rays which are received at the detector element edge region.

Although the post-patient collimators in the twin beam scanner described above may block the x-rays from the adjacent edges of adjacent detector elements in respective rows, the x-rays may still be received within such detector element edge regions. In addition, use of collimators and detector elements arranged in respective adjacent detector rows may reduce the dose efficiency of the system since at least the projection data represented in the attenuated x-ray beam portions which are blocked by the collimators is lost. Further, due to the detector characteristics at the detector edge region, the projection data represented in the attenuated x-ray received at the detector edge region does not facilitate reconstructing an image of high quality. Such non-uniformity in the detector response at the edges typically results in the generation of artifacts when a sloped object is scanned.

In addition to the projection data discontinuities, calibrating such a twin beam scanner also is difficult. Particularly, although the x-ray source may be initially correctly aligned so that an output x-ray is centered to be received in substantially equal portions by adjacent detector cells, an x-ray may become off-centered during a scan operation. For example, as the x-ray source heats up, the thermal expansion of the anode may cause the focal spot to move. Also, as the gantry rotates, mechanical stresses on the gantry and x-ray source may cause additional focal spot motion. Such movement of the x-ray focal spot is particularly troublesome with the twin beam scanner described above since such movement may result in an increase in the percentage of an x-ray received in the edge region of a detector element. If such an increase occurs during a scan, the initial calibration for the detector element may be incorrect, and such a condition may result in additional artifacts being generated.

Known twin beam systems may be utilized to perform a helical scan. To perform a helical scan, the object to be imaged is moved along the z-axis while the gantry rotates. In a twin beam system, double interwoven helixes are mapped by the projection data. In a helical scan, if a helical pitch of about or equal to 1:1 is selected, a significant amount of "overlap" may occur. Specifically, a 1:1 helical pitch means that the table increment in one gantry rotation equals the width of one slice. The projection data collected by one detector element in the first row may substantially overlap, or be substantially identical to, the projection data collected by an adjacent detector element in the second row in the next gantry rotation. Such overlap is undesirable because the duplicate projection data does not significantly facilitate generating images for multiple slices.

Accordingly, it would be desirable and advantageous to provide twin beam scanner which facilitates collecting projection data within a detector element region which provides a more uniform sensitivity response than the detector edge region and which substantially eliminates projection data overlap in a helical scan. It would also be desirable and advantageous to provide such a scanner which does not generate projection data discontinuities and may be more easily calibrated.

SUMMARY OF THE INVENTION

These and other objects may be attained with a twin beam computed tomography system which, in one embodiment, includes an x-ray source, an x-ray detector array having adjacent rows of detector cells positioned to receive x-rays emitted from the x-ray source, and a dynamic pre-patient collimator positioned so that the x-ray projected from the x-ray source is substantially split to form at least two beams prior to being projected at least partially through the object to be imaged.

The system further includes, in one embodiment, an offset detector data acquisition system, a reference detector data acquisition system, a motor controller and a motor. The data acquisition systems are coupled to receive inputs from the detector array, and outputs from the data acquisition systems are coupled to the motor controller. The motor controller controls operation of the motor, which may be a stepper motor.

The pre-patient collimator includes, in one embodiment, a housing, a beam splitting member secured to housing by a rotatable shaft, and first and second collimating members. The distance between the first and second collimating members is adjustable. The beam splitting member is partially positioned between the first and second collimating members and, in the one embodiment, is rotatable relative the collimating members. The rotatable shaft and collimating members are coupled to the motor which controls the position of the beam splitting member and the collimators.

Prior to scanning, and after a helical pitch has been selected, the motor operates to position the collimating members and beam splitting member in positions determined to be preferred for the selected helical pitch. Such positions may be predetermined through experimentation and prestored in the motor controller memory. Typically, the orientation of the beam splitter and collimating members are selected, for a helical scan, to avoid data overlap.

In one form of operation, a beam emitted from the x-ray source is received at the pre-patient collimator. The pre-patient collimator, or beam splitter, splits the input beam to form two output beams which are then at least partially attenuated through an object to be imaged. The transmitted portions of the two beams are received by the detector cells.

Signals from the detector cells are provided to the offset detector data acquisition system and the reference detector data acquisition system. These signals indicate the position of the fan beams relative to the detector cells and are utilized by the motor controller to control the position of the beam splitting member during a scan. Specifically, under the control of the motor controller, the stepper motor adjusts the position of the beam splitting member relative to the first and second collimators so that the beams output from the pre-patient collimator impinge on the detector cells in a desired location, e.g., not in the detector edge regions.

The above described scanner facilitates collecting projection data within a detector cell region which provides a more uniform sensitivity response than the detector edge region and may substantially eliminate projection data overlap in a helical scan. Such scanner also facilitates more accurate detector calibration and can be controlled so that projection data discontinuities may be substantially eliminated.

DETAILED DESCRIPTION

Figure 1:
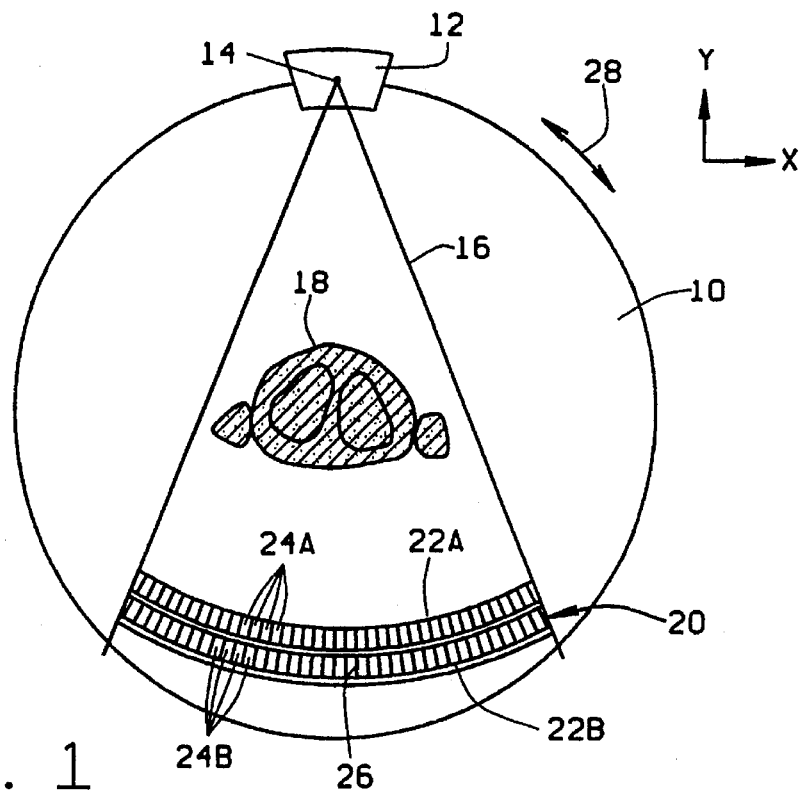
FIG. 1 is a schematic representation of an x-ray source and an x-ray detector of a twin beam scanner.

Referring to FIG. 1, a gantry 10, representative of a "third generation" computed tomography scanner type, includes an x-ray source 12 having a focal spot 14. A fan beam of x-rays 16 are emitted from source 12 towards an object 18 to be imaged. A detector array 20, composed of two rows 22A and 22B of detector elements or cells 24A and 24B and collimators 26, is mounted on a side of gantry 10 opposing x-ray source 12. Source 12 and detector array 20 rotate on gantry 10 as indicated by arrow 28.

Figure 2:
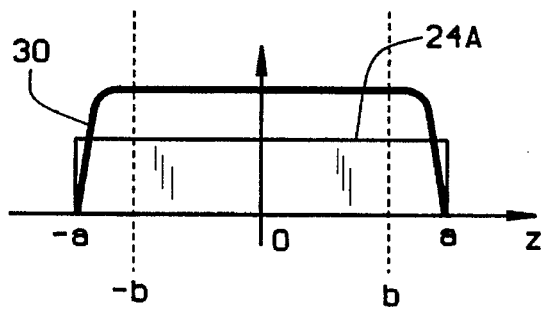
FIG. 2 illustrates the detector sensitivity response curve with respect to a detector element.

FIG. 2 illustrates a typical detector sensitivity response curve 30 with respect to detector element 24A. Detector element 24A is shown positioned axially with respect to the z-axis, with the center of detector element 24A indicated by the "0" point on the z-axis and the respective ends, or edges, of detector element 24A located at points "a" and "−a" respectively As clearly shown by curve 30, at both edges of detector 24A, the sensitivity response of detector element 24A is extremely low and has significant variation as function of position.

Points "b" and "−b" represent the locations where, moving axially along z-axis towards the detector edges, the detector element sensitivity about begins to fall off. Detector element 24A may not generate highly accurate intensity indicative signals for x-rays received at or between points a and b and points −a and −b, respectively. The detector edge regions are generally defined as the portions of detector element 24A between and including points a and b and points −a and point −b.

Figure 3:
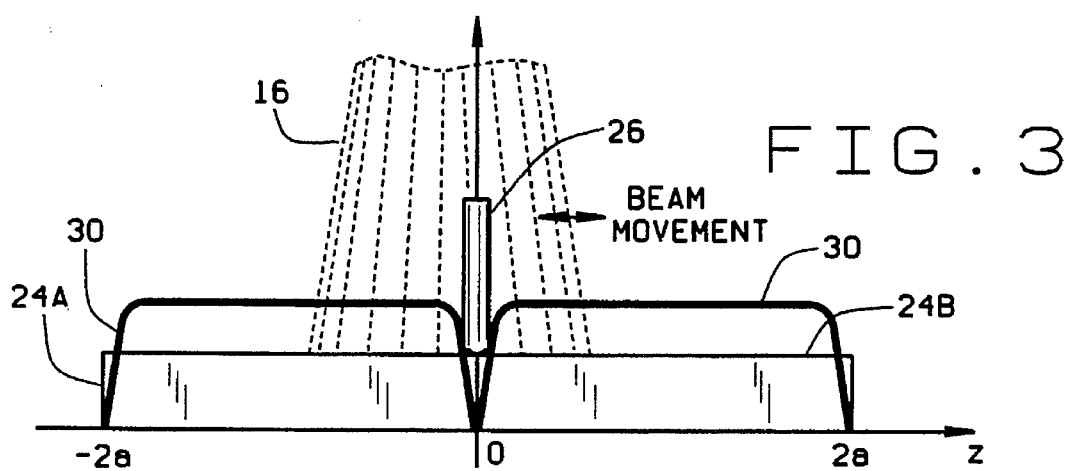
FIG. 3 illustrates an x-ray impinging upon adjacent detector elements in a twin beam scanner having only a post-patient collimator and respective detector sensitivity response curves.

FIG. 3 illustrates adjacent detector elements 24A and 24B of detector array 20, collimator 26 and x-ray beam 16. Collimator 26 may be constructed of x-ray absorbing material such as sintered molybdenum, and is utilized to substantially block a portion of beam 16 from substantially impinging upon adjacent edges of detectors 24A and 24B.

Beam 16 is illustrated as being off-center with respect to the center axis of collimator 26. As described above, such a condition may result from focal spot movement. Regardless of the cause, it can be seen in FIG. 3 that a greater percentage of beam 16 is received in the edge region of detector element 24B when beam 16 is off-center as shown. Such a condition may result in the generation of artifacts. Also, even though collimator 26 may block a portion of beam 16 from impinging upon sections of the edge regions of detectors 24A and 24B, at least some portions of beam 16 are still received within such edge regions. As explained above, such a condition is undesirable.

Figures 4A, 4B:
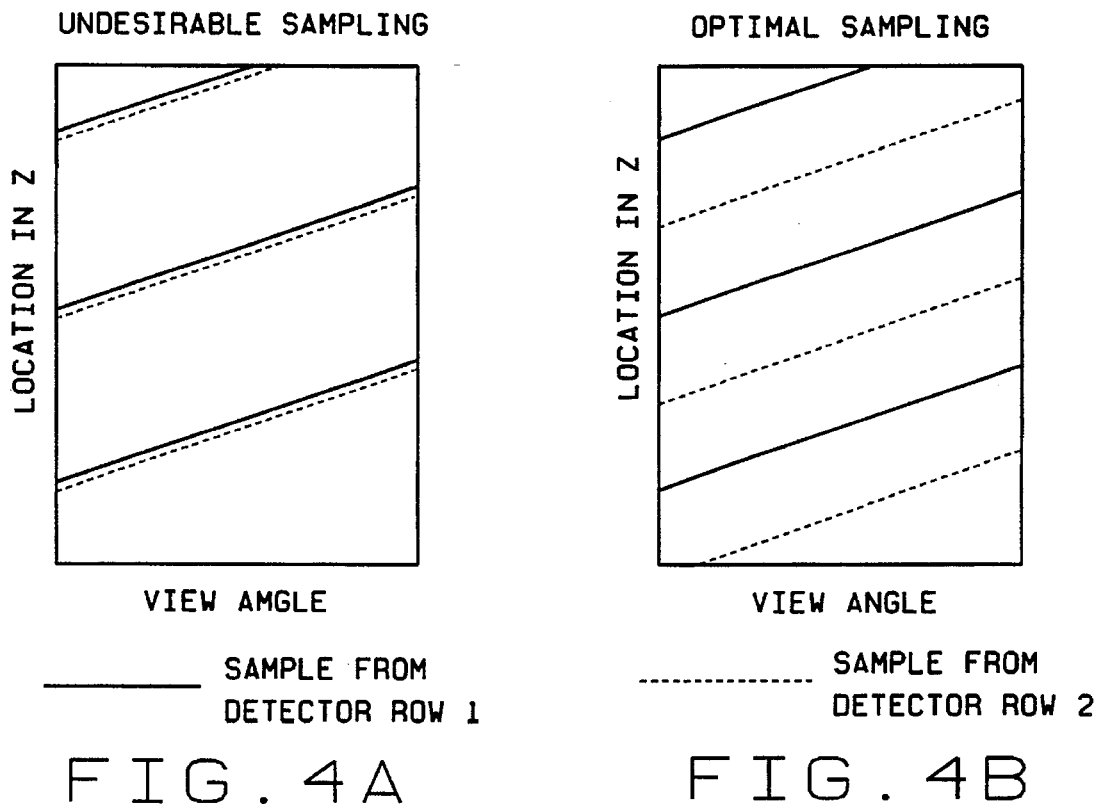
FIG. 4A illustrates possible projection data sampling in a twin beam scanner having only a post-patient collimator with a near 1:1 helical pitch
FIG. 4B illustrates the optimal projection data sampling.

FIG. 4A illustrates projection data sampling in a twin beam scanner having a post-patient collimator with a helical pitch about equal to 1:1, and FIG. 4B illustrates the optimal projection data sampling. As shown in FIG. 4A, double interwoven helixes mapped by the projection data have a significant amount of "overlap". This means that the projection data collected by one detector element in the first row substantially overlaps, or is substantially identical to, the projection data collected by an adjacent detector element in the second row in the next gantry rotation. Such overlap is undesirable because the duplicate projection data does not significantly facilitate generating higher quality images for multiple slices.

FIG. 4B illustrates the optimal projection data sampling by adjacent detectors in separate detector rows. Particularly, as shown in FIG. 4B, there is no significant overlap and the projection data collected by the detector elements in the second row straddle the samples by the detector elements in the first row. Providing such sampling increases the amount of projection data collected and should improve the quality of an image reconstructed using such data.

Figure 5:
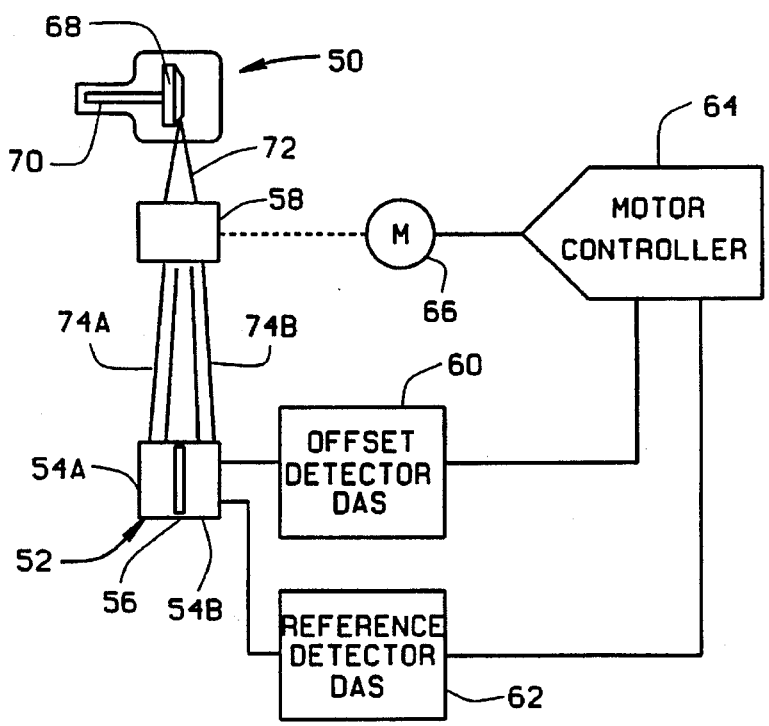
FIG. 5 is a schematic representation of an x-ray source, an x-ray detector and a dynamic pre-patient collimator.

FIG. 5 is a schematic representation of an x-ray source 50, an x-ray detector array 52 having at least two adjacent rows of detector cells 54A and 54B separated by a collimator 56, and a dynamic pre-patient collimator 58. An offset detector data acquisition system 60 and a reference detector data acquisition system 62 are coupled to detector array 52, and outputs from such systems 60 and 62 are supplied to a motor controller 64. Motor controller 64 drives a stepper motor 66 which is coupled to pre-patient collimator 58.

X-ray source 50 includes an anode 68 and a rotating shaft 70 and operates in a well known manner. For a third generation system, X-ray source 50, pre-patient collimator 58 and detector array 52 would be mounted to the system gantry (not shown) in the one embodiment.

Prior to operation, and for a plurality of selectable helical pitches, the particular orientations for components of collimator 58 are determined. For example, the components, which are hereinafter described in more detail, should be oriented in a first configuration for a first helical pitch and in a second configuration for a second helical pitch. The selected orientations may be determined, for example, by experimentation to avoid any significant data overlap.

In one form of operation, a beam 72 emitted from source 50 is received at pre-patient collimator, or beam splitter, 58. Splitter 58 is configured, as hereinafter described in more detail, so that input beam 72 is split and forms two output beams 74A and 74B. Beams 74A and 74B are then at least partially attenuated through an object to be imaged, and the transmitted portions of beams 74A and 74B are received by detector array 52.

Signals from detector array 52 are collected by an imaging system (not shown) and may be used to reconstruct an image of the object. In addition, signals from array 52 are received by an offset detector data acquisition system 60 and a reference detector data acquisition system 62. More specifically, as is well known in the art, a z-axis offset detector (not shown) and a reference detector (not shown) may be utilized to detect the fan beam position and supply inputs to systems 60 and 62, respectively. Such fan beam detection is described, for example, in U.S. Pat. No. 4,559,639, X-Ray Detector With Compensation Height-Dependant Sensitivity And Method Of Using Same, issued Dec. 17, 1985 and assigned to the assignee of the present invention, and incorporated herein, in its entirety, by reference.

Signals received by DAS 60 and 62 are digitized and output to motor controller 64. Motor controller 64, using such digitized signals, determines whether an adjustment is necessary in order to better position beams 72A and 72B on the respective detector cells 54A and 54B, e.g., not on the detector edge regions. If adjustment is necessary, a control signal is supplied from controller 64 to stepper motor 66. Under the control of controller 64, stepper motor 66 adjusts splitter 58 so that beams 72A and 72B are positioned on cells 54A and 54B as desired. Such adjustment is referred to herein as dynamic adjustment of splitter 58 in that such adjustment may be made during a scan operation.

Figure 6:
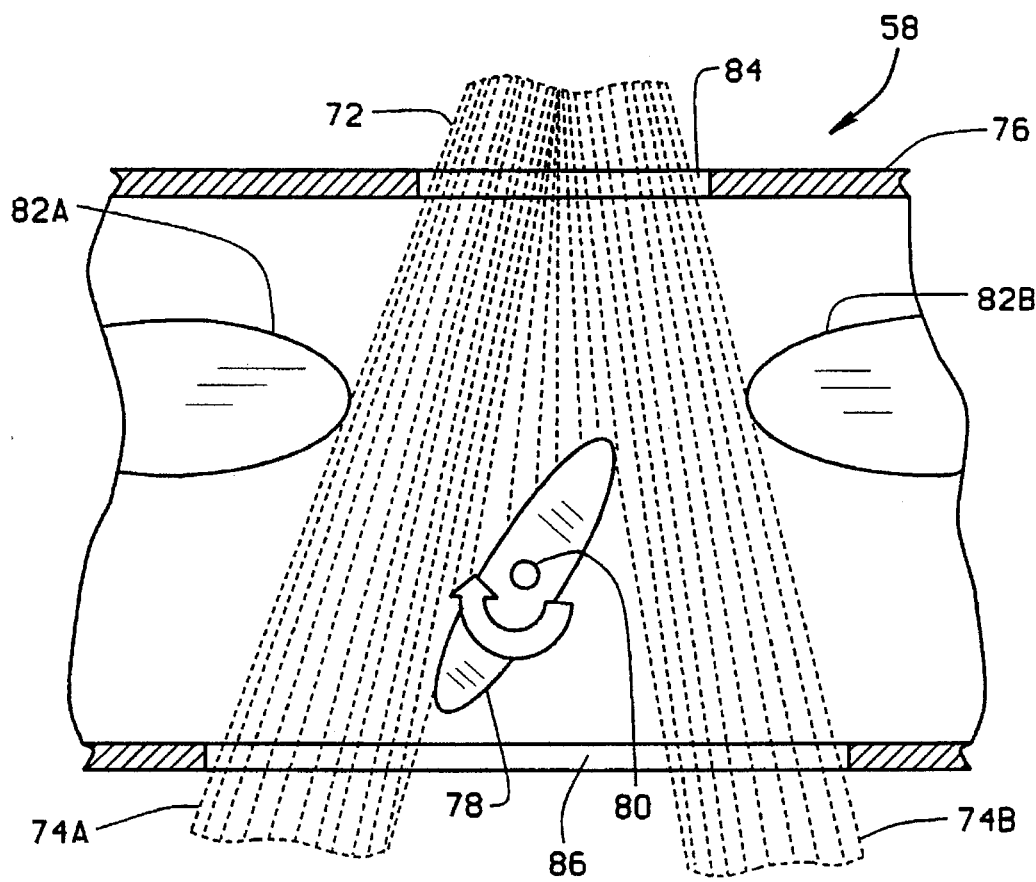
FIG. 6 illustrates, in more detail and in cross section, the dynamic pre-patient collimator shown in FIG. 5.

One embodiment of splitter or pre-patient collimator 58 is shown in cross section in FIG. 6. Splitter 58 includes a housing 76, a beam splitting member 78 rotatably secured to housing 76 utilizing a rotatable shaft 80, and first and second collimating members 82A and 82B. Beam splitting member 78 is at least partially positioned between first and second collimating members 82A and 82B and is rotatable relative such members 82A and 82B. Beam splitting member 78 also has an elongate elliptical shape, and collimators 82A and 82B and beam splitting member 78 are constructed of x-ray absorbing material such as molybdenum. Housing 76 includes an input beam opening 84 and output beams opening 86.

Rotatable shaft 80 is coupled to stepper motor 66, and motor 66 controls the position of beam splitting member 78 relative to collimators 82A and 82B as described above. First and second collimating members 82A and 82B also may be coupled to stepper motor 66 so that the distance between members 82A and 82B may be adjusted. Specifically, by adjusting beam splitting member 78 and collimating members 82A and 82B to a desired position, the relative positions of output beams 74A and 74B may be adjusted.

Figure 7:
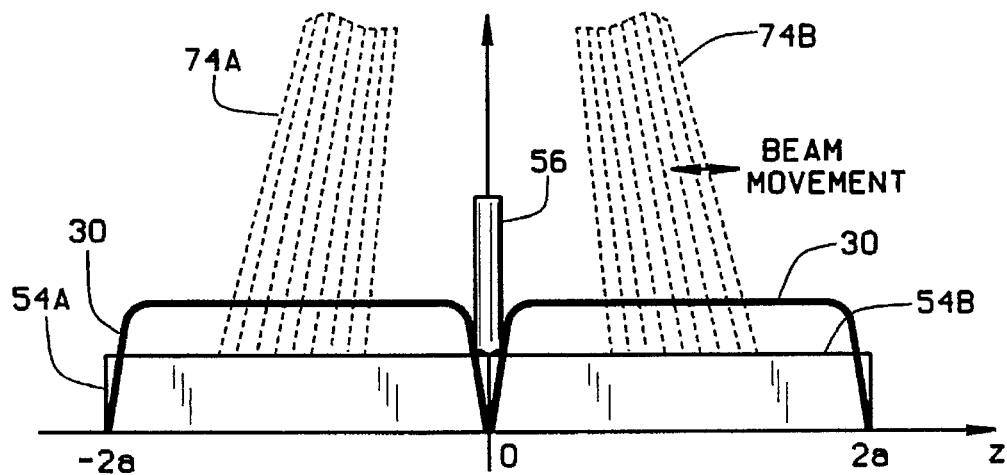
FIG. 7 illustrates x-rays impinging upon adjacent detector elements in a twin beam scanner having a dynamic pre-patient collimator, and respective detector element sensitivity response curves.

FIG. 7 illustrates x-rays 74A and 74B impinging upon adjacent detector elements 54A and 54B in a twin beam scanner having dynamic pre-patient collimator 58, and respective detector element sensitivity response curves 30. As shown in FIG. 7, both beams 74A and 74B impinge on detector cells 54A and 54B in the relatively flat region of the detector sensitivity response curve 30 for the respective cells 54A and 54B.

Beam splitting member 78 and collimating members 82A and 82B generally are positioned, based on the selected helical pitch, so that optimal sampling, as shown in FIG. 4B, may be obtained. As described above, the preferred positioning for members 78, 82A and 82B may be determined through experimentation for various helical pitches and stored in the motor controller memory.

In addition, by dynamically adjusting beam splitting member 78, beams 74A and 74B may be maintained within such flat curve regions during a scan. Such dynamic adjustment provides the desirable result that more accurate projection data may be collected. In addition, such adjustment facilitates eliminating projection data overlap in a helical scan.

Further, in one form of operation, no portion of the x-ray attenuated through the object to be imaged is blocked by collimator 56, and no x-rays are received in the detector edge regions. Such a configuration facilitates eliminating projection data discontinuities and accurately calibrating the imaging system.

It should be understood, of course, that the shape of beam splitting member 78 and collimators 82A and 82B are not limited to the shapes shown in FIG. 6. For example, member 78 may have many different shapes, including even shapes in which member 78 is not symmetrical about its axis of rotation. Also, although it may be preferable in some configurations, beam splitting member 78 does not necessarily have to be dynamically adjustable. Rather, it is contemplated that sufficient advantages could be obtained by adjusting member 78 prior to a scan and maintaining member 78 in a fixed position for at least one scan.

As one specific example of an alternative configuration, it is contemplated that the beam splitting member may have a triangular shape with the apex of the triangular beam splitting member positioned to be the first portion of the splitting member to intercept a transmitted x-ray beam. The axial location, relative to the center axis of symmetry, of the beam splitting member is adjustable so that the relative angular orientation between the output beams is adjustable. Rather than being rotationally adjustable, the triangular shaped beam splitting member is axially adjustable, and such axial adjustment controls certain characteristics, e.g., spacing, of the output beams. Of course, the triangular shaped beam splitting member could also be rotatable to provide additional degrees of adjustment.

From the preceding description of several embodiments of the present invention, it is evident that the objects of the invention are attained. Although the invention has been described and illustrated in detail, it is to be clearly understood that the same is intended by way of illustration and example only and is not to be taken by way of limitation. For example, the beam splitter described herein could be utilized with many other computed tomography system, such as "fourth generation"

systems in which a stationary detector array extends fully around the gantry bore and only the x-ray source and splitter rotate with the gantry. Accordingly, the spirit and scope of the inventions are to be limited only by the terms of the appended claims.

What is claimed is:

1. A twin beam computed tomography scanner for performing a helical scan, comprising:

an x-ray source for generating an x-ray to be projected generally towards, and at least partially through, an object;

a detector array comprising a plurality of detector cells, said cells arranged to form at least two cell rows;

a beam splitter positioned so that the x-ray projected from said x-ray source is substantially split to form at least two beams prior to being projected at least partially through the object;

a data acquisition system coupled to said detector array; and a controller coupled to said data acquisition system and to said beam splitter for controlling said beam splitter so that the x-ray beams from said beam splitter do not substantially impinge on edge regions of said detector cells.

2. A scanner in accordance with claim 1 wherein said detector cells are arranged so that a first edge of a first cell in a first cell row is adjacent a first edge of a first cell in a second cell row.

3. A scanner in accordance with claim 2 wherein each of said detector cells comprises at least a first edge region in which the sensitivity response of said detector cell is lower than the sensitivity response with respect to at least one other cell location.

4. A scanner in accordance with claim 3 wherein a collimator is positioned so as to substantially block x-rays from impinging on said first edges of said first and second cells.

5. A scanner in accordance with claim 1 wherein said beam splitter comprises a beam splitting member configured to cause a first input beam to be split into at least two output beams.

6. A scanner in accordance with claim 5 wherein said beam splitting member is constructed of x-ray absorbing material.

7. A scanner in accordance with claim 5 wherein said beam splitter further comprises first and second collimating members, said beam splitting member at least partially positioned in a beam path which extends between said first and second collimating members.

8. A scanner in accordance with claim 7 wherein said beam splitting member is movable relative to at least one of said collimating members.

9. A scanner in accordance with claim 5 wherein said beam splitting member has an elongate elliptical shape and is rotatable relative to at least one of said collimating members.

10. A scanner in accordance with claim 5 wherein said beam splitting member has a triangular shape.

11. A scanner in accordance with claim 5 further comprising first and second spaced collimating members, the relative orientations of said first and second collimating members and said beam splitting member being selectively adjustable based on a helical pitch.

12. A method of generating projection data for an object using a scanner having a beam splitter, an x-ray source and an x-ray detector array having at least two rows of detector cells, each detector cell having at least one edge region, said method comprising the steps of:

projecting an x-ray beam from the source towards the object and through the beam splitter as the source rotates around the object and as the object moves axially relative to the source along a z-axis;

detecting whether any beam impinges upon an edge region of a detector cell; and if a beam impinges upon the edge region of a detector cell, then adjusting the beam splitter so that the beams do not substantially impinge upon the detector cell edge region.

13. A method in accordance with claim 12 wherein the beam splitter includes first and second collimating members and a beam splitting member, and the relative orientation of the first and second collimating members and the beam splitting member is selected substantially based on helical pitch.

14. A method in accordance with claim 12 further comprising the step of collimating the x-ray beam prior to the beam being at least partially projected through the object.

15. A computed tomography system for performing a helical scan and for generating an image of an object, said system comprising an x-ray source, an x-ray detector array having adjacent rows of detector cells positioned to receive x-rays emitted from said x-ray source, and a pre-patient collimator positioned so that the x-ray projected from said x-ray source is substantially split to form at least two beams prior to being projected at least partially through the object to be imaged, said system further comprising an offset detector data acquisition system, a reference detector data acquisition system, a motor controller and a motor, said data acquisition systems coupled to said detector array, outputs from said data acquisition systems coupled to said motor controller, said motor being coupled to said pre-patient collimator and configured to control said pre-patient collimator so that the x-ray beams from said pre-patient collimator do not substantially impinge on edge regions of said detector cells.

16. A computed tomography system in accordance with claim 15 wherein said pre-patient collimator comprises a housing, a beam splitting member, and first and second collimating members.

17. A computed tomography system in accordance with claim 16 wherein said beam splitting member is movable relative to said collimating members.

* * * * *